(12) United States Patent
Bak et al.

(10) Patent No.: US 10,609,882 B1
(45) Date of Patent: Apr. 7, 2020

(54) NEOREGELIA CULTIVAR NAMED 'BLUZH'

(71) Applicant: Corn Bak BV, Assendelft (NL)

(72) Inventors: Elly Bak, Rijsenhout (NL); Nicolaas Steur, Oude Niedorp (NL)

(73) Assignee: Corn. Bak, BV (NL)

( * ) Notice: Subject to any disclaimer, the term of this patent is extended or adjusted under 35 U.S.C. 154(b) by 0 days.

(21) Appl. No.: 16/431,940

(22) Filed: Jun. 5, 2019

(51) Int. Cl.
*A01H 6/22* (2018.01)
*A01H 5/10* (2018.01)

(52) U.S. Cl.
CPC ................. *A01H 5/10* (2013.01); *A01H 6/22* (2018.05)

(58) Field of Classification Search
CPC ....................................................... A01H 6/22
USPC ........................................................... Plt./370
See application file for complete search history.

(56) References Cited

U.S. PATENT DOCUMENTS

PP27,212 P2 * 9/2016 Bullis ..................... A01H 6/22
Plt./370

* cited by examiner

*Primary Examiner* — David H Kruse
(74) *Attorney, Agent, or Firm* — Cassandra Bright

(57) ABSTRACT

A new and distinct *Neoregelia* cultivar named 'BLUZH' characterized by its low and spreading rosette, plant size measuring about 45 cm in diameter; glossy green-colored lower leaves overlain with red colored (closest to RHS 66C) uppermost leaves and long-lasting habit.

5 Claims, 1 Drawing Sheet
(1 of 1 Drawing Sheet(s) Filed in Color)

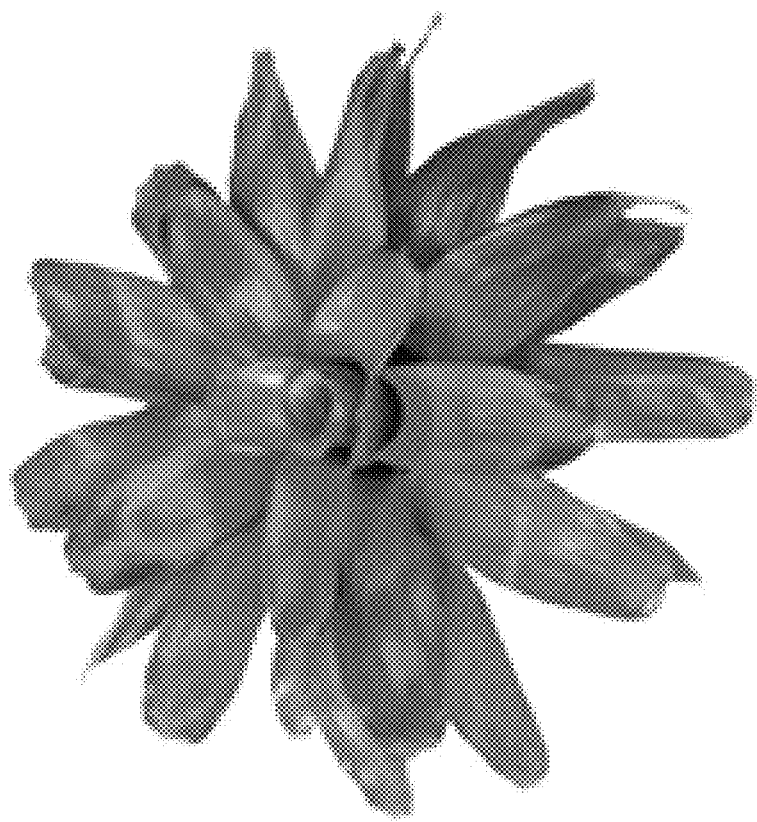

NEOREGELIA CULTIVAR NAMED 'BLUZH'

FIELD OF THE INVENTION

The present invention relates to a new, distinct and stable cultivar of *Neoregelia*, hereinafter referred to as 'BLUZH'. The present invention relates to seeds which are the *Neoregelia* 'BLUZH', as well as, plants and plant parts produced by these seeds which have all of the morphological and physiological characteristics of the *Neoregelia* cultivar. The present invention also relates to methods for producing these seeds and plants of the *Neoregelia* cultivar 'BLUZH'. Furthermore, the present invention relates to a method of producing progeny *Neoregelia* plants by crossing *Neoregelia* 'BLUZH', as either the female or seed or male or pollen parent, with another *Neoregelia* plant and selecting progeny.

BACKGROUND OF THE INVENTION

The present invention relates to a new, distinct and stable cultivar, botanically known as *Neoregelia carolinae*, and hereinafter referred to by the variety denomination 'BLUZH'. The new *Neoregelia* 'BLUZH' originated from a cross made in a controlled breeding program by the inventors in 2013, and then first flowered in 2015, in Assendelft, The Netherlands. The female or seed parent is an unnamed proprietary selection of *Neoregelia carolinae* identified by code 1309410321 (unpatented). The male or pollen parent is an unnamed proprietary selection of *Neoregelia carolinae* identified by code 1309410320 (unpatented). The objective of the breeding program is to create new *Neoregelia* plants with uniquely colored leaves.

*Neoregelia* is member of the Bromeliaceae family. *Neoregelia* is epiphytic and native to the tropics. For the most part species have stemless inflorescences and flowers that barely rise above the water in the center of the plants.

Leaves of *Neoregelia* are mostly broad and relatively flat. The inner leaves of *Neoregelia* are often brightly colored. The colour ranges from green, white and various shades of red through to purple.

A need exists for a greater variety of *Neoregelia* cultivars with attractive ornamental features. Additionally, a need exists for additional *Neoregelia* cultivars that can be easily propagated by seed.

The new *Neoregelia* 'BLUZH' was developed through a controlled breeding program and exhibits unique, desirable and stable characteristics.

SUMMARY OF THE INVENTION

The present invention provides *Neoregelia* plant selections that are solid, medium-sized, long-lasting cultivar with uniquely colored leaves that exhibits good keeping quality.

These and other objectives have been achieved in accordance with the present invention which provides 'BLUZH' as a new *Neoregelia* cultivar that is a product of a planned breeding program conducted by the inventors, Elly Bak and Nico D. M. Steur, in Assendelft, The Netherlands, in 2013. The female or seed parent is an unnamed proprietary selection of *Neoregelia carolinae* identified by code 1309410321 (unpatented). The male or pollen parent is an unnamed proprietary selection of *Neoregelia carolinae* identified by code 1309410320 (unpatented).

Both parental cultivars have a sufficient degree of homozygosity such that the progeny of the cross are genetypically and phenotypically uniform. The new cultivar 'BLUZH' therefore can be produced by sexual reproduction by crossing the parental selections identified by the codes 1309410321 and 1309410320 to produce a population of progeny plants, each of which has the combination of characteristics as herein disclosed for the new variety 'BLUZH'.

Seeds which are the cultivar 'BLUZH' are produced by crossing the parental selections identified by the codes 1309410321 and 1309410320, and are deposited with the NCIMB limited, Ferguson Building, Craibstone Estate, Bucksburn, Aberdeen, AB21 9YA, United Kingdom. NCIMB accession number 43382. 2500 seeds were deposited with the NCIMB on Apr. 25, 2019.

OBJECTS OF THE INVENTION

The present invention relates to seeds which produce *Neoregelia* 'BLUZH'. The present invention also relates to *Neoregelia* plants, and parts thereof, having all the physiological and morphological characteristics of *Neoregelia* 'BLUZH'. The present invention relates to a plant produced from seeds which are *Neoregelia* 'BLUZH'. The present invention also relates to plant parts, such as pollen, seeds or inflorescence produced by *Neoregelia* 'BLUZH'.

The present invention relates to a method of producing seed which are *Neoregelia*, by a crossing *Neoregelia carolinae* selection identified by code 1309410321 (unpatented) as the female or seed parent with *Neoregelia carolinae* selection identified by code 1309410320 (unpatented) as the male or pollen parent and the reciprocate cross with 1309410320 (unpatented) as the female or seed parent and 1309410321 (unpatented) as the male parent and harvesting seeds produced from said cross.

The present invention also relates to a method of producing plants having all the physiological and morphological characteristics of the *Neoregelia* 'BLUZH' comprising the steps of (a) crossing *Neoregelia carolinae* selection identified by code 1309410321 (unpatented) as a female or seed parent with *Neoregelia carolinae* selection identified by code 1309410320 (unpatented) as the male or pollen parent. (b) harvesting seeds produced from said cross; and (c) producing plants from said harvested seeds.

BRIEF DESCRIPTION OF THE PHOTOGRAPH

The patent or application file contains at least one drawing executed in color. Copies of this patent or patent application publication with color drawings will be provided by the Office upon request and payment of the necessary fees.

The accompanying photograph illustrates the overall appearance of the new *Neoregelia* cultivar 'BLUZH' showing the colors as true as is reasonably possible with colored reproductions of this type. Colors in the photograph may differ slightly from the color values cited in the detailed botanical description which accurately describes the color of 'BLUZH'.

The accompanying drawing shows an overhead view perspective of a typical potted plant of 'BLUZH', at 13 months of age from potting size.

DETAILED BOTANICAL DESCRIPTION

The present invention was created by the inventors, Elly Bak and Nicolaas D. M. Steur in 2013 and flowered for the first time in 2015 in Assendelft, The Netherlands.

This invention is directed to *Neoregelia* plant having all the morphological and physiological characteristics of the cultivar 'BLUZH' produced from seeds which are the product of the cross of the *Neoregelia carolinae* selection identified by code 1309410321 (unpatented) as the female or seed parent with the *Neoregelia carolinae* selection identified by code 1309410320 (unpatented) as the male or pollen parent. Both parents have a sufficient degree of homozygosity such that the progeny of the cross were, and continue to be, phenotypically uniform. The new cultivar 'BLUZH' can therefore be produced by sexual reproduction by crossing of the *Neoregelia carolinae* selections identified by the codes 1309410321 and 1309410320 to produce a population of progeny plants, each of which has the combination of characteristics herein disclosed for the new cultivar 'BLUZH'.

The new cultivar 'BLUZH' can also be produced by asexually reproducing progeny from the cross of the parental inbred lines identified by the codes 1309410321 and 1309410320. Asexual reproduction of the new cultivar by vegetative means by cuttings was first performed in 2015 in Assendelft, The Netherlands. The first 'BLUZH' plants propagated through the use of such cuttings flowered in 2016 in Assendelft, The Netherlands, and have demonstrated that the new cultivar reproduces true-to-type and that the combination of characteristics as herein disclosed for the new cultivar are firmly fixed and retained through successive generations of asexual reproduction.

BRIEF DESCRIPTION OF THE INVENTION

The following traits have been repeatedly observed and are determined to be unique characteristics of 'BLUZH' which in combination distinguish this *Neoregelia* as a new and distinct cultivar:

1. The plant habit is a low and spreading rosette;
2. The innermost leaves at the center of the rosette are red (closest to RHS 66C)
3. 'BLUZH' has a finely serrated leaf margin;
4. Long-lasting habit.

The most similar in comparison to the new *Neoregelia* 'BLUZH' is the specie *Neoregelia carolinae*. Plants of the new cultivar 'BLUZH' differ from plants of *Neoregelia carolinae* primarily in color of the uppermost leaves at the center of the rosette.

'BLUZH' has not been tested and observed under all possible environmental conditions. The phenotype of the new cultivar may vary with variations in environment such as temperature, light intensity, frequency of fertilization, composition of fertilizer, flowering treatment, day length and humidity, without any change in the genotype of the plant.

For example, substantial differences in plant height and diameter, number of leaves, can result depending on the size of the plant at the time that flowering is induced by flowering treatment. Since treatment to induce flowering disrupts normal watering and fertilization regimens. Flowering treatment of relatively smaller plants adversely affects the growth of the plant.

The aforementioned photographs, together with the following observations, measurements and values describe the new *Neoregelia carolinae* 'BLUZH' as grown in a greenhouse in Assendelft, The Netherlands, under conditions which closely approximate those generally used in commercial practice. Plants of 'BLUZH' were grown in a greenhouse with day temperatures ranging from 20° C. to 28° C. and night temperatures ranging from 18° C. to 23° C. No artificial lighting or photoperiodic treatments were conducted, but plants of 'BLUZH' are forced into flowering.

Color references are made to the Royal Horticultural Society Color Chart (RHS), 2001 edition, except where general colors of ordinary significance are used. Color values were taken under daylight conditions in a greenhouse in Assendelft, The Netherlands. The age of the plants of 'BLUZH' described is about 10 weeks after flowering treatment.

Classification:
Botanical: *Neoregelia carolinae*.
Parentage:
  Female Parent: Unnamed proprietary *Neoregelia carolinae* selection identified by code 1309410321 (unpatented)
  Male Parent: Unnamed proprietary *Neoregelia carolinae* selection identified by code 1309410320 (unpatented)
Plant:
General Appearance and Form:
  Height: About 10.5 cm (when flowering)
  Width: About 45 cm
  Shape: Flattened Funnel form rosette
  Growth habit: Upright and outwardly arching growth habit. Rosette leaves are erect when young, becoming outwardly arching with development.
  Plant Vigor: Good
  Flowering Season: A fully grown plant can flower year round, starting 10 weeks after induction of natural light or through flowering treatment.
  Cold Tolerance: Frost tender. Temperatures below 5° C. may damage plants.
  Fragrance: None
Foliage:
  Arrangement: Rosette, sessile
  Shape: Oblong
  Apex: Cuspidate
  Base: Truncate
  Margin: finely serrated
  Quantity: About 26 (depending on the size of the plant)
  Size of Leaf:
    Length: About 8 cm (when flowering)
    Width mid-section: About 4 cm
    Width base: About 6 cm
    Texture, upper and lower surfaces: Smooth
    Luster, upper and lower surfaces: Glossy
  Color: Leaf color can vary somewhat depending on growing conditions.
  Lower leaves: upper surface: green, closest to 137A under surface: green, RHS closest to 137B
  Uppermost leaves: upper surface: red, closest to RHS 66C Under surface: red, closest to RHS 67B
  Color of uppermost leaves intensify during flowering.
  Venation: None
Inflorescence:
  Form: compound head nestled in the center of the rosette. About 100 flowers per inflorescence
  Size:
    Diameter: about 4-5 m
  Time of Bloom: A fully grown plant can bloom the whole year starting about 10 weeks after induction or through flowering treatment.
  Flowering is not commercially important in 'BLUZH'
  Duration of Bloom: Each flower last one day.
  Flower size:
    Length: about 3.5 cm
    Diameter: about 0.8 cm Petals:
  Quantity per flower: 3
  Shape: linear spatulate
  Apex: acute
  Margin: entire
  Length: about 3.5 cm
  Width: about 0.7 cm
  Texture: smooth
  Color: white, closest to 155 D, towards the apex blue violet, closest to 88B
Reproductive Organs:
Stamens:
  Number: 6 per flower
  Filament length: about 2.4 cm
  Filament color: Near RHS White 155D
  Anther color: Near Yellow-White 158B
Pistils:
Quantity per flower: one
Stigma color: Yellow-White 158A
Style length: about 2.3 cm
Style color: Near RHS White 155D
Ovary color: Near RHS White 155D
Seeds/Fruit:
Fruit and seed production have not been observed on plants of *Neoregelia* 'BLUZH'.

Disease/Pest Resistance:
Not observed to date.
Disease/Pest Susceptibility:
Not observed to date.

We claim:

1. A *Neoregelia carolinae* plant named 'BLUZH', representative seed having been deposited at the NCIMB in Aberdeen, Scotland, NCIMB accession number 43382.

2. A *Neoregelia* seed that produces the *Neoregelia carolinae* plant of claim 1.

3. A plant part obtained from the *Neoregelia carolinae* plant of claim 1.

4. A method of producing *Neoregelia* progeny plant comprising the steps of
  (a) crossing a *Neoregelia carolinae* plant of variety 'BLUZH' as the female or male parent, representative seed having been deposited at the NCIMB in Aberdeen, Scotland under NCIMB accession number 43382, with a second *Neoregelia* plant, and
  (b) selecting progeny.

5. The method according to claim 4, wherein the second *Neoregelia* plant is 'BLUZH'.

\* \* \* \* \*